(12) United States Patent
Giatti et al.

(10) Patent No.: US 6,770,189 B2
(45) Date of Patent: Aug. 3, 2004

(54) PROCESS FOR IMPROVING THE PURITY OF QUATERNARY AMMONIUM HYDROXIDES BY ELECTROLYSIS

(75) Inventors: Anna Giatti, Arnhem (NL); Fred Korpel, Roosendaal (NL); Roger Keranen Rains, Richfield, OH (US); Gerrit Jan Boerman, Deventer (NL)

(73) Assignee: Flexsys B.V., Deventer (NL)

( * ) Notice: Subject to any disclaimer, the term of this patent is extended or adjusted under 35 U.S.C. 154(b) by 220 days.

(21) Appl. No.: 09/981,140

(22) Filed: Oct. 16, 2001

(65) Prior Publication Data

US 2002/0079233 A1 Jun. 27, 2002

Related U.S. Application Data

(60) Provisional application No. 60/248,811, filed on Nov. 15, 2000.

(30) Foreign Application Priority Data

Oct. 27, 2000 (EP) .............................. 00203744

(51) Int. Cl.[7] .............................. B01D 61/44
(52) U.S. Cl. ................ 205/688; 205/703; 205/437; 204/530
(58) Field of Search ................ 205/688, 703, 205/437; 204/541, 522, 530, 537

(56) References Cited

U.S. PATENT DOCUMENTS

| | | | | |
|---|---|---|---|---|
| 3,402,115 | A | | 9/1968 | Campbell et al. ............ 204/180 |
| 4,714,530 | A | | 12/1987 | Hale et al. ................... 204/131 |
| 5,389,211 | A | | 2/1995 | Sharifian et al. .............. 204/72 |
| 5,910,237 | A | * | 6/1999 | Moulton et al. ............. 204/541 |
| 5,951,845 | A | | 9/1999 | Moulton ...................... 205/746 |
| 6,207,039 | B1 | * | 3/2001 | Moulton et al. ............. 205/703 |

FOREIGN PATENT DOCUMENTS

JP 03020489 * 1/1991

OTHER PUBLICATIONS

Patent Abstracts of Japan of Japanese Patent Publication No.: 63213686.
Patent Abstracts of Japan of Japanese Patent Publication No.: 03020489.
Derwent Abstract No: XP–002165656.
Derwent Abstract No: XP–002165657.
European Search Report for EP 00 20 3744 dated Apr. 20, 2001.

* cited by examiner

Primary Examiner—Arun S. Phasge
(74) Attorney, Agent, or Firm—Louis A. Morris

(57) ABSTRACT

The present invention relates to a process for improving the purity of a composition comprising a quaternary ammonium hydroxide comprising the steps of (a) providing an electrolysis cell which comprises an anolyte compartment containing an anode, a catholyte compartment containing a cathode, and at least one intermediate compartment, said at least one intermediate compartment being separated from the anolyte and catholyte compartments by cation selective membranes, (b) charging water, optionally containing a supporting electrolyte, to the anolyte compartment, charging water, optionally containing a quaternary ammonium hydroxide, to the catholyte compartment, and charging the composition comprising the quaternary ammonium hydroxide to be purified to the intermediate compartment, (c) passing a current through the electrolysis cell to produce a purified aqueous quaternary ammonium hydroxide solution in the catholyte compartment, and (d) recovering the purified aqueous quaternary ammonium hydroxide solution from the catholyte compartment. The process is particularly suitable for improving the purity of an aqueous solution comprising tetramethylammonium hydroxide which has been used in the production of 4-aminodiphenylamine for a number of reaction cycles.

20 Claims, No Drawings

PROCESS FOR IMPROVING THE PURITY OF QUATERNARY AMMONIUM HYDROXIDES BY ELECTROLYSIS

CROSS REFERENCE TO RELATED APPLICATIONS

This application claims priority from EP 00203744.8, filed Oct. 27, 2000 and U.S. Provisional Application No. 60/248,811, filed Nov. 15, 2000, the contents of both applications incorporated herein in their entirety.

BACKGROUND OF THE INVENTION

1. Field of the Invention

The present invention relates to a process for improving the purity of a composition comprising a quaternary ammonium hydroxide.

2. Prior Art

Quaternary ammonium hydroxides such as tetramethylammonium hydroxide (TMAH) are used inter alia as a developer for photoresists in the manufacture of printed circuit boards and microelectronic chips and as a base in the production of 4-aminodiphenylamine (4-ADPA). Alkylated derivatives of 4-ADPA such as N-(1,3-dimethylbutyl)-N'-phenyl-p-phenylenediamine (6PPD) are used as anti-degradants in rubber compositions and rubber articles such as tires.

In said production of 4-ADPA, the base—which typically is in the form of an aqueous solution—is recycled many times (hereinafter also referred to as recycle base). However, after a certain number of reaction cycles, the active content of the aqueous base solution has decreased to such an extent that it can no longer be used in the production process and either some of the recycle aqueous base solution is purged and replaced with fresh base solution or all of it is discarded as waste, which adds to the cost of the 4-ADPA and the 6PPD prepared therefrom. The present invention provides a solution to this waste problem. Also, with an increasing number of reaction cycles, the liquid-liquid separation of the aqueous base solution from the 4-ADPA-containing organic phase proceeds with greater difficulty.

When TMAH is used as the base, the purged/discarded aqueous recycle base solution contains inter alia various tetramethylammonium (TMA) salts, such as tetramethylammonium acetate, formate, chloride, carbonate, and oxalate as well as aniline—one of the starting materials for preparing 4-ADPA. It further contains small amounts of various other salts and other organic impurities.

Quaternary ammonium hydroxides are typically prepared by means of electrolysis. For example, TMAH may be prepared from tetramethylammonium chloride using a two-compartment electrolysis cell comprising an anolyte compartment containing an anode and a catholyte compartment containing a cathode, said compartments being separated by a cation selective membrane. Said membrane is also referred to in the art as a cation-exchange membrane. In this manufacturing process, the quaternary ammonium salt from which the quaternary ammonium hydroxide is prepared is charged to the anolyte compartment of the electrolysis cell.

It is also known in the art to improve the purity of mixtures comprising a quaternary ammonium hydroxide by electrolysis.

For example, U.S. Pat. No. 4,714,530 discloses a process for producing high-purity quaternary ammonium hydroxides by means of electrolysis using a two-compartment electrolysis cell equipped with a cation-exchange membrane in which an aqueous solution containing the quaternary ammonium hydroxide is charged to the anolyte compartment.

U.S. Pat. No. 5,389,211 discloses a process for improving the purity of organic or inorganic hydroxides such as quaternary ammonium hydroxides by means of electrolysis using an electrolysis cell comprising at least one intermediate compartment which is separated from the anolyte and catholyte compartments by at least two nonionic dividers and/or cation selective membranes. The mixture containing the hydroxide is charged to the anolyte compartment. It is mentioned that the catholyte and intermediate compartments may also contain organic or inorganic hydroxide prior to initiation of the electrolysis. It is mentioned that the purpose of charging purified hydroxide to the intermediate compartment is to avoid the build-up of impurities in that compartment (col. 12, ll. 47–51).

The processes of U.S. Pat. Nos. 4,714,530 and 5,389,211 relate to improving the purity of in particular aqueous waste solutions of quaternary ammonium hydroxides which have been used as a developer for photoresists in printed circuit boards and microelectronic chips, which solutions typically contain significant amounts of halogen. The waste aqueous solutions comprising quaternary ammonium hydroxides which are obtained during the production of 4-ADPA, however, generally do not have a similarly high halogen content; they typically contain other anions as described above and organic impurities, in particular aniline.

SUMMARY OF THE INVENTION

In its primary embodiment, the present invention comprises a process for improving the purity of a composition comprising a quaternary ammonium hydroxide in comprising the steps of:

(a) providing an electrolysis cell which comprises an anolyte compartment containing an anode, a catholyte compartment containing a cathode, and at least one intermediate compartment, said at least one intermediate compartment being separated from the anolyte and catholyte compartments by cation selective membranes, (b) charging water, optionally containing a supporting electrolyte, to the anolyte compartment, charging water, optionally containing a quaternary ammonium hydroxide, to the catholyte compartment, and charging the composition comprising the quaternary ammonium hydroxide to be purified to the intermediate compartment, (c) passing a current through the electrolysis cell to produce a purified aqueous quaternary ammonium hydroxide solution in the catholyte compartment, and (d) recovering the purified aqueous quaternary ammonium hydroxide solution from the catholyte compartment.

Other embodiments of the invention encompass various other streams charged to the electrolysis cell and their compositions, use of a three-component electrolysis cell, process conditions and details, types of cation selective membranes employed, all of which are hereinafter disclosed in the following discussion of each of the facets of the present invention.

DETAILED DESCRIPTION OF THE INVENTION

We have found that the electrolysis of recycle TMAH—obtained from the production of 4-ADPA—by charging it to the anolyte compartment of a two-compartment electrolysis cell soon after its start resulted in the formation of a significant amount of a solid material at the anode, which fouled the electrode and the anolyte compartment and virtually stopped the electrolysis after some time (see Comparative Examples A and B).

Surprisingly, we subsequently found that these problems were less severe or even did not occur when the electrolysis was carried out in accordance with the present invention.

In the case of recycle base which is obtained from the production of 4-ADPA, the invention process results in the recovery from the catholyte compartment of an aqueous solution containing lower amounts of anions, such as acetate, formate, chloride, carbonate, and oxalate, than are present in the recycle base and, if desired, having a higher quaternary ammonium hydroxide content. Typically, the recovered aqueous base solution also contains a portion/fraction of the neutral organic compounds such as aniline which are present in the recycle base.

Due to the fact that the anolyte and catholyte compartments contain aqueous solutions, oxygen gas is formed at the anode and hydrogen gas is formed at the cathode. The presence of tetramethylammonium carbonate and/or tetramethylammonium bicarbonate in the intermediate compartment may cause the formation of carbon dioxide gas, which depends on the pH of the aqueous solution in the intermediate compartment. These gases are handled and processed in a conventional way.

The invention process can be carried out using any known electrolysis cell equipped with conventional electrodes and cation selective membranes, provided said electrodes and membranes are compatible with the solutions which are charged to and which are formed in the anolyte, intermediate, and catholyte compartments.

The anode and the cathode may be made from a variety of materials. The anode must be suitable for oxygen formation/evolution and the cathode for hydrogen formation/evolution. Suitable anodes and cathodes are known to a person of ordinary skill in the art. The cathode may also be an oxygen reducing/oxygen depolarized cathode. Preferably, a dimensionally stable anode (DSA) for oxygen evolution and a stainless steel cathode are used.

The cation selective membranes may be any of those that have been used in the electrolysis of quaternary ammonium salts to quaternary ammonium hydroxides and the electrolytic purification of quaternary ammonium hydroxides. A variety of suitable cation selective membranes are available to a person of ordinary skill in the art. A distinction is made between perfluorinated and non-perfluorinated membranes. Preferably, the cation selective membranes to be used in accordance with the present invention are perfluorinated membranes, for example made from polytetrafluoroethylene, such as the ones sold under the name Nafion by DuPont. Other suitable cation selective membranes include membranes made from polyethylene, polypropylene, polyvinylchloride, polystirene-divinylbenzene, and (sulfonated) polysulfone.

Apart from the fact that cation selective membranes allow the passage of cations and prevent the transport of anions, said membranes are also selective for the type of cation. For example, in the art proton selective membranes are known.

In the invention process, at least two cation selective membranes are used. These membranes may be identical or not. It is practical to use two identical cation selective membranes. Preferably, the invention process is carried out using a proton selective membrane, separating the anolyte compartment from the intermediate compartment, and a membrane selective for the quaternary ammonium ion which is present in the composition comprising the quaternary ammonium hydroxide to be purified, separating the intermediate compartment from the catholyte compartment.

The electrolysis cell to be used in the invention process contains at least one intermediate compartment. Hence, the cell contains three or more compartments, the compartments each being separated by cation selective membranes as described above. Preferably, a three-compartment electrolysis cell is used, since the use of more than two cation selective membranes increases the cost of the electrolysis cell as well as the consumption of electricity, i.e. it increases the cost of operation. Generally, the inclusion of additional cation selective membranes will result in an increase in the purity of the aqueous quaternary ammonium hydroxide solution recovered from the catholyte compartment.

If a high-purity aqueous quaternary ammonium hydroxide solution is desired and consequently two or more intermediate compartments are used, in accordance with the invention process the composition comprising the quaternary ammonium hydroxide to be purified is charged to that intermediate compartment which is immediately next to the anolyte compartment. In that case, the other intermediate compartment(s) and catholyte compartment typically will contain aqueous quaternary ammonium hydroxide solutions of high purity, e.g., of the desired purity.

The quaternary ammonium hydroxide-containing compositions which are purified in accordance with the process of the present invention typically are aqueous solutions containing from 1 to 45, preferably 5 to 40, more preferably 10 to 35 wt % of quaternary ammonium hydroxide. These compositions may contain an organic solvent. They may also contain an inorganic hydroxide such as sodium hydroxide, potassium hydroxide or cesium hydroxide.

The quaternary ammonium hydroxide-containing composition to be used in the process of the present invention may contain any quaternary ammonium hydroxide. Typically, the composition comprises a tetrahydrocarbylammonium hydroxide or hydrocarbylene di(trihydrocarbyl)ammonium dihydroxide. The composition may also comprise a mixture of a quaternary ammonium hydroxide and an inorganic hydroxide. Typical examples include tetramethylammonium hydroxide, tetrapropylammonium hydroxide, tetrabutylammonium hydroxide, choline hydroxide, phenyltrimethylammonium hydroxide, benzyltrimethylammonium hydroxide, and bis-dibutylethyl hexamethylene diammonium hydroxide (hexamethylene 1,6-di(dibutylethyl)ammonium dihydroxide). Other suitable examples have been described in the prior art cited above, i.e. U.S. Pat, No. 4,714,530 (col. 2, I. 60 through col. 3, I. 2) and U.S. Pat. No. 5,389,211 (col. 5, II. 43–60). Preferably, the composition comprises tetramethylammonium hydroxide (TMAH). More preferably, the composition to be purified in accordance with the present invention is an aqueous solution which has been used in the production of 4-ADPA for a number of reaction cycles (i.e. recycle base), most preferably, an aqueous solution comprising TMAH. The recycle base typically contains aniline. The recycle base may also contain an inorganic hydroxide.

At the start of electrolysis, the anolyte compartment contains water, optionally containing a supporting electrolyte, and the catholyte compartment contains water, optionally containing a quaternary ammonium hydroxide. Preferably, demineralized or soft water is used in the invention process. The term "supporting electrolyte" is known to the person skilled in this art. Any supporting electrolyte may be used. The supporting electrolyte is present mainly to increase the conductivity of the anolyte solution. In the catholyte compartment, the increase in conductivity of the catholyte solution is performed by including a quaternary ammonium hydroxide. The presence of electrolytes in the anolyte and catholyte compartments allows current to flow through the electrolysis cell immediately after the start of the electrolysis. It is to be noted that it is not critical to the invention process which electrolyte—containing aqueous solutions are present in the anolyte and catholyte compartments. Their choice will mainly be determined by the desired purity and the desired active content of the aqueous quaternary ammonium hydroxide solution to be recovered from the catholyte compartment. Preferably, the desired active content is in the range of 15 to 25 wt %, more preferably about 20 wt %.

Preferably, the anolyte solution contains a supporting electrolyte. More preferably, the anolyte compartment contains an aqueous solution of a strong acid such as sulfuric acid or phosphoric acid, most preferably sulfuric acid. A practical anolyte solution to start with is an aqueous 1 to 10, preferably 3 to 9, more preferably 3 to 5 wt % sulfuric acid solution. Preferably, the volume (i.e. water is consumed during the electrolysis and transported towards the catholyte compartment), the active content, and the level of impurities in the aqueous solution present in the anolyte compartment are monitored, and the volume and the active content are adjusted when necessary. If the level of impurities becomes undesirably high, the entire anolyte solution may be discarded and replaced with a fresh solution.

Preferably, the catholyte compartment contains an aqueous solution of a quaternary ammonium hydroxide which is the same as the quaternary ammonium hydroxide present in the composition to be purified. A practical catholyte solution to start with is an aqueous 1 to 35, preferably 5 to 25, more preferably 5 to 20 wt % solution of the quaternary ammonium hydroxide. Preferably, the catholyte compartment is charged with an aqueous quaternary ammonium hydroxide solution of high purity, e.g., a solution having the desired purity. The active content may vary as desired. More preferably, an aqueous TMAH solution is used as the starting catholyte solution.

The invention process may be carried out batchwise or as a semi-continuous or continuous process. It is practical to use a batch process. Preferably, the invention process is carried out by charging a batch of the composition comprising the quaternary ammonium hydroxide to be purified to the intermediate compartment and continuing the electrolysis until practically all of the quaternary ammonium ions are removed therefrom before charging a subsequent batch to the intermediate compartment. In the case of recycle base, it was found to be advantageous to dilute the recycle base with water before charging it to the intermediate compartment of the electrolysis cell. The processed batch—present in the intermediate compartment—may either be discarded wholly or partly and is then replaced by or the remainder is mixed with the subsequent batch, respectively. In the case of recycle base, preferably a part of the processed batch—i.e. the so-called heel—is mixed with a fresh portion of recycle base. More preferably, about equal weight parts of heel and fresh recycle base are charged to the intermediate compartment.

In a preferred embodiment of the invention process, the intermediate compartment is washed with a suitable solvent. It was found that some solid material was formed in the intermediate compartment after processing a number of batches. As a result, fouling of the membrane separating the anolyte compartment from the intermediate compartment and of the intermediate compartment fluid circulation equipment, i.e. the circulation loop, loop filter, and circulation vessel, occurred. Suitable solvents are those which dissolve the solid material that is formed without affecting any part of the electrolysis equipment. This can easily be determined by a person of ordinary skill in the art. Suitable solvents include aniline, N,N-dimethylformamide, N-methyl-2-pyrrolidone, and dimethyl sulfoxide. In the case of recycle base, preferably aniline is used as the solvent. This washing step is carried out as frequently and using as much of the solvent as necessary. Again, this can easily be determined by a person of ordinary skill in the art. In the case of a batchwise operation of the invention process, it is practical to perform the washing at the end of the processing of each batch. Preferably, after washing with a suitable solvent, the intermediate compartment is washed with water before charging a new batch to the intermediate compartment. In the case of recycle base and when using aniline as the solvent, it is best to remove the aniline by washing with water afterwards.

The solvent washing step typically is carried out at an elevated temperature, preferably 40 to 80, more preferably 40 to 60, most preferably 40 to 50° C. The washing with water typically is carried out at a temperature of 20 to 50° C.

The electrolysis of the composition comprising the quaternary ammonium hydroxide to be purified is effected by applying a direct current between the anode and the cathode with a current density of generally up to 4,000 A/m$^2$. A practical range is from 500 to 1,500 A/m$^2$. The current is applied to the electrolysis cell for a period of time sufficient to allow for the transport of preferably all quaternary ammonium ions from the intermediate compartment to the catholyte compartment. An important parameter for monitoring the progress of the invention process is the pH of the aqueous solution in the intermediate compartment.

During the electrolysis of the composition comprising the quaternary ammonium hydroxide to be purified and when, for example, an aqueous sulfuric acid solution is used as the anolyte, the pH of the solution of the intermediate compartment decreases due to the transport of protons from the anolyte compartment to the intermediate compartment and the transport of quaternary ammonium ions from the intermediate compartment to the catholyte compartment. Anions such as chloride ions are unable to pass the cation selective membrane separating the intermediate compartment from the catholyte compartment. A weak acid such as acetic acid, however, is able to pass a cation selective membrane by way of diffusion. Preferably, the electrolysis is stopped once a pH of 1 to 7, more preferably 4 to 7, even more preferably 4 to 6, most preferably about 5 is reached in the intermediate compartment.

In the case of recycle base obtained from the production of 4-ADPA, and in case the invention process is carried out batchwise, the pH in the intermediate compartment decreases from a value of higher than 10 to any desired final pH value. If only a part of the processed composition—present in the intermediate compartment—is replaced by a subsequent batch, or when the process is carried out as a continuous operation, the pH may be maintained between certain chosen values, e.g., between 5 and 7.

Typically, the aqueous solutions present in each of the compartments of the electrolysis cell are circulated by means of pumping in a conventional way, for example, by using circulation loops, circulation vessels, and pumps for each compartment separately. These circulation loops may be provided with filters.

During the electrolysis, the temperature of the solutions within the compartments typically is maintained at from 10 to 90, preferably 40 to 80, more preferably 40 to 60, most preferably 40 to 50° C.

The present invention is illustrated by the following Examples.

EXAMPLES 1 and 2

Two one-batch experiments were performed using a three-compartment Micro Flow Cell (from ElectroCell) comprising an anolyte compartment containing an anode, a catholyte compartment containing a cathode, and an intermediate compartment being separated from the anolyte and catholyte compartments by two cation selective membranes. EPDM gaskets and Teflon frames were used.

In the first experiment, i.e., Example 1, two Nafion 117 membranes (from DuPont) were used. The anode at the start of the experiment was platinum, later it was replaced with a dimensionally stable anode (DSA) for oxygen evolution (both from ElectroCell). The cathode was stainless steel (from ElectroCell). The anolyte solution was changed several times as a result of which on average it contained 2.17 wt % aqueous $H_2SO_4$ and 4.59 wt % aqueous acetic acid (HAc) and the amount of tetramethylammonium (TMA)-acetate in the intermediate compartment increased. The starting catholyte solution was 6.7 wt % aqueous tetramethylammonium hydroxide (TMAH). The recycle base contained 12.85 wt % TMAH and was charged to the intermediate compartment of the electrolysis cell.

In the second experiment, i.e., Example 2, two Nafion 324 membranes (from DuPont) were used. The anode was a DSA for oxygen evolution, the cathode stainless steel. The anolyte was 2.50 wt % aqueous $H_2SO_4$, the catholyte was 4.94 wt % aqueous TMAH. The recycle base contained 19.90 wt % TMAH and was charged to the intermediate compartment.

The results depicted in Tables 1–3 show that the electrolysis of recycle TMAH results in a considerable purification of the base in that the amounts of TMA-acetate, TMA-formate, TMA-chloride, $TMA_2$-carbonate, and $TMA_2$-oxalate in the aqueous solution recovered from the catholyte compartment are considerably lower than in the solution present in the intermediate compartment, and that the TMAH content in the aqueous solution that is recovered from the catholyte compartment has increased notably while leaving no TMAH in the intermediate compartment. Additionally, some aniline is present in the aqueous solution which is recovered from the catholyte compartment.

The detection limits are as follows: TMA-acetate (0.0023 wt %), TMA-formate (0.0013 wt %), TMA-chloride (0.0015 wt %), $TMA_2$-carbonate (0.0350 wt %), $TMA_2$-oxalate (0.0027 wt %), and TMAH (0.0100 wt %).

TABLE 1

Electrolysis data

|  | Example 1 | Example 2 |
|---|---|---|
| Average current efficiency (%) | 32 | 60 |
| Average current density (A/m$^2$) | 700 | 450 |
| Temperature (° C.) | 45 | 45 |
| Final pH intermediate compartment | 5.2 | 1.1 |
| DC Voltage (V) | 7 | 7.5 |

TABLE 2

Starting and recovered base compositions

| Example 1 |  | $A_{start}$ | $A_{final}$ | $I_{start}$ | $I_{final}$ | $C_{start}$ | $C_{final}$ |
|---|---|---|---|---|---|---|---|
| TMA-Acetate | wt % |  |  | 0.86 | 4.44 | nd | 0.06 |
| TMA-Formate | wt % |  |  | 1.34 | 1.05 | nd | 0.04 |
| TMA-Chloride | wt % |  |  | 0.03 | 0.003 | nd | 0.002 |
| $TMA_2$-Carbonate | wt % |  |  | 11.55 | 0.61 | nd | 0.49 |
| $TMA_2$-Oxalate | wt % |  |  | 2.05 | 1.58 | nd | 0.02 |
| TMAH | wt % |  |  | 12.85 | nm | 6.7 | 24.0 |
| Aniline | wt % |  |  | 1.33 | 0.35 | nd | 0.59 |
| $H_2SO_4$ | wt % | 2.17 | nd |  |  |  |  |
| Hac | wt % | 4.59 | nd |  |  |  |  |
| Weight | g | 3536.8 | 3030.9 | 832.6 | 722.7 | 726.8 | 765.2 |
| Samples taken | g |  |  |  | 179.2 |  | 164.9 |

$A_{start}$ is the starting solution in the anolyte compartment, $A_{final}$ is the final anolyte solution, $I_{start}$ is the starting solution in the intermediate compartment, $I_{final}$ is the final solution in the intermediate compartment, $C_{start}$ is the starting catholyte solution, and $C_{final}$ is the final catholyte solution, TMA represents tetramethylammonium, nm means not measurable (below the detection limit), nd means not determined.

TABLE 3

Starting and recovered base compositions

| Example 2 |  | $A_{start}$ | $A_{final}$ | $I_{start}$ | $I_{final}$ | $C_{start}$ | $C_{final}$ |
|---|---|---|---|---|---|---|---|
| TMA-Acetate | wt % |  |  | 1.23 | 1.45 | nd | 0.05 |
| TMA-Formate | wt % |  |  | 0.83 | 1.00 | nd | 0.08 |
| TMA-Chloride | wt % |  |  | 0.02 | 0.003 | nd | 0.002 |
| $TMA_2$-Carbonate | wt % |  |  | 9.65 | 0.64 | nd | 0.23 |
| $TMA_2$-Oxalate | wt % |  |  | 1.55 | 2.05 | nd | 0.02 |
| TMAH | wt % |  |  | 19.90 | nm | 4.94 | 25.6 |

TABLE 3-continued

Starting and recovered base compositions

| Example 2 | | $A_{start}$ | $A_{final}$ | $I_{start}$ | $I_{final}$ | $C_{start}$ | $C_{final}$ |
|---|---|---|---|---|---|---|---|
| Aniline | wt % | | | 2.68 | nd | nd | nd |
| $H_2SO_4$ | wt % | 2.50 | 3.03 | | | | |
| Weight | g | 790.6 | 408.2 | 932.6 | 438.2 | 607.2 | 954.1 |
| Water added | g | 50.7 | | 323.0 | | | |
| Samples taken | g | | 213.0 | | 318.9 | | 186.2 |

$A_{start}$ is the starting solution in the anolyte compartment, $A_{final}$ is the final anolyte solution, $I_{start}$ is the starting solution in the intermediate compartment, $I_{final}$ is the final solution in the intermediate compartment, $C_{start}$ is the starting catholyte solution, and $C_{final}$ is the final catholyte solution, TMA represents tetramethylammonium, nm means not measurable (below the detection limit), nd means not determined.

Comparative Examples A and B

Two one-batch experiments were performed using a two-compartment Micro Flow Cell (from ElectroCell) comprising an anolyte compartment containing an anode and a catholyte compartment containing a cathode, said compartments being separated by means of a cation selective membrane. EPDM gaskets and Teflon frames were used.

In the first experiment, i.e. Comparative Example A, a Nafion 450 membrane (from DuPont) was used. The anode was a platinum electrode, the cathode stainless steel. The recycle base was charged to the anolyte compartment and it contained 13.61 wt % TMAH. The starting catholyte solution was 13.85 wt % aqueous TMAH.

In the second experiment, i.e. Comparative Example B, a Nafion 117 membrane was used. The anode was a DSA for oxygen evolution, the cathode stainless steel. The recycle base was charged to the anolyte compartment and it contained 12.68 wt % TMAH, the catholyte was 12.09 wt % aqueous TMAH. The results of these experiments are shown in Tables 4 to 6.

It was found that at the anode a significant amount of a solid material was formed which fouled the electrode and the anolyte compartment and had to be removed periodically in order to be able to continue the electrolysis. Ultimately, the electrolysis virtually stopped ($TMA^+$ bound to carbonate was not transported from the anolyte to the catholyte compartment). As a result, the electrolysis could not be performed long enough for an economically attractive recovery of TMAH to be obtained. In addition, the removal of this solid was time consuming and cumbersome.

TABLE 4

Electrolysis data

| | Comparative Example | |
|---|---|---|
| | A | B |
| Average current efficiency (%) | 35 | 19 |
| Average current density (A/m²) | 1300 | 2400 |
| Temperature (° C.) | 46 | 47 |
| DC Voltage (V) | 7.7 | 8.2 |

TABLE 5

Starting and recovered base compositions

| Comp. Ex. A | | $A_{start}$ | $A_{final}$ | $C_{start}$ | $C_{final}$ |
|---|---|---|---|---|---|
| TMA-Acetate | wt % | 0.74 | 0.66 | nm | nm |
| TMA-Formate | wt % | 1.09 | 1.02 | nm | nm |
| TMA-Chloride | wt % | 0.02 | 0.02 | nm | nm |
| $TMA_2$-Carbonate | wt % | 12.08 | 18.18 | 0.16 | 0.32 |
| $TMA_2$-Oxalate | wt % | 1.89 | 1.43 | nm | nm |
| TMAH | wt % | 13.61 | 0.33 | 13.85 | 21.98 |
| Aniline | wt % | 1.90 | 0.44 | nd | 0.24 |
| Weight | g | 900 | 830 | 750 | 420 |
| Water added | g | 100 | | | |
| Samples taken | g | | 240 | | 240 |

$A_{start}$ is the starting anolyte solution, $A_{final}$ is the final anolyte solution, $C_{start}$ is the starting catholyte solution, and $C_{final}$ is the final catholyte solution, nm means not measurable (below the detection limit), nd means not determined.

TABLE 6

Starting and recovered base compositions

| Comp. Ex. B | | $A_{start}$ | $A_{final}$ | $C_{start}$ | $C_{final}$ |
|---|---|---|---|---|---|
| TMA-Acetate | wt % | 0.67 | 1.08 | nm | nm |
| TMA-Formate | wt % | 1.06 | 1.25 | nm | nm |
| TMA-Chloride | wt % | 0.02 | 0.02 | nm | nm |
| $TMA_2$-Carbonate | wt % | 13.25 | 24.98 | nm | nm |
| $TMA_2$-Oxalate | wt % | 1.86 | 1.65 | nm | nm |
| TMAH | wt % | 12.68 | nm | 12.09 | 23.44 |
| Aniline | wt % | 1.79 | 0.56 | nd | 0.47 |
| Weight | g | 900 | 570 | 750 | 530 |
| Water added | g | 100 | | | |
| Samples taken | g | | 120 | | 120 |

$A_{start}$ is the starting anolyte solution, $A_{final}$ is the final anolyte solution, $C_{start}$ is the starting catholyte solution, and $C_{final}$ is the final catholyte solution, nm means not measurable (below the detection limit), nd means not determined.

EXAMPLE 3

A three-compartment Multi Purpose Cell (from ElectroCell) equipped with a DSA anode, a stainless steel cathode, and two Nafion 324 cation selective membranes was operated, according to a procedure similar to the procedure described in Examples 1 and 2 (i.e. 12.5 V, 40–50° C., final pH 5), with 42 batches of recycle base for a total (electrolysis) time of 1,095 h. Each time, the composition to be electrolyzed consisted of a mixture of 1,600 g of fresh recycle base, having a composition similar to the compositions described in Examples 1 and 2, and 1,600 g of the so-called heel of the previously processed batch of recycle base (i.e. each batch having a total weight of 3,200 g), and 700 g of the heel were discarded. At the end of the processing of each batch, the purified aqueous TMAH solution was recovered from the catholyte compartment and the intermediate compartment including the fluid circulation loop and circulation vessel were emptied and the circulation vessel was filled with 1,000 g of aniline. The aniline was circulated for 30 min through the intermediate compartment at a temperature of 50° C. Then, the aniline wash was removed and the wash procedure was repeated with 1,000 g of water, which was circulated for 5 min at a temperature of 20–50° C., the water being warmed up during circulation. After each washing procedure, the next 3,200 g batch of recycle base plus heel was charged to the intermediate compartment and subjected to electrolysis.

The capacity of the electrolysis cell remained practically unchanged, i.e. it was 24.31 moles $TMA^+/m^2/h$ for the first batch and 24.99 moles $TMA^+/m^2/h$ for the forty-secondth batch ($TMA^+$ stands for tetramethylammonium ion). Inspection of the electrolysis cell after the processing of the 42 batches did not show any fouling of the membrane separating the anolyte compartment from the intermediate compartment.

Comparative Example C

A three-compartment Multi Purpose Cell equipped with a DSA anode, a stainless steel cathode, and two Nafion 324 cation selective membranes was operated, according to a procedure similar to the procedure described in Examples 1 and 2 (i.e. 12.5 V, 40–50° C., final pH 5), with 25 batches of recycle base for a total (electrolysis) time of 450 h. Each the composition to be electrolyzed consisted of a mixture of 1,600 g of fresh recycle bas,e having a composition similar to the compositions describes in Examples 1 and 2, and 1,600 g of the so-called heel of the previously processed batch of recycle base (i.e. each batch having a total weight of 3,200 g), and 700 of the heel were discarded.

The capacity of the electrolysis ell had dropped from 27.75 moles $TMA^+/m^2/h$ for the first batch to less than 6 moles $TMA^+/m^2/h$ for the twenty-fifth batch. Inspection of the electrolysis cell after the the processing of the 25 batches learned that the membrane separating the anolyte compartment from the intermediate compartment was fouled and that solids were present in the aqueous solution of the intermediate compartment and in connected liquid circulation system, i.e. intermediate compartment circulation loop, loop filter, and circulation vessel.

What is claimed is:

1. A process for improving the purity of a composition comprising a quaternary ammonium hydroxide contained in a recycle stream obtained from the production of 4-aminodiphenylamine comprising the steps of
(a) providing an electrolysis cell which comprises an anolyte compartment containing an anode, a catholyte compartment containing a cathode, and at least one intermediate compartment, said at least one intermediate compartment being separated from the anolyte and catholyte compartments by cation selective membranes,
(b) charging water, optionally containing a supporting electrolyte, to the anolyte compartment, charging water, optionally containing a quaternary ammonium hydroxide, to the catholyte compartment, and charging the composition comprising said recycle stream to be purified to the intermediate compartment,
(c) passing a current through the electrolysis cell to produce a purified aqueous quaternary ammonium hydroxide solution in the catholyte compartment, and
(d) recovering the purified aqueous quaternary ammonium hydroxide solution from the catholyte compartment.

2. The process of claim 1 wherein the anolyte compartment is charged with an aqueous solution of a strong acid.

3. The process of claim 1 wherein the anolyte compartment is charged with an aqueous 1 to 10 wt % sulfuric acid solution.

4. The process of claim 1 wherein the intermediate compartment is charged with an aqueous solution comprising tetramethylammonium hydroxide (TMAH).

5. The process of claim 1 wherein the intermediate compartment is charged with an aqueous solution containing 5 to 40 wt % of TMAH.

6. The process of claim 1 wherein the intermediate compartment is charged with an aqueous solution comprising TMAH which has been used in the production of 4-aminodiphenylamine for a number of reaction cycles.

7. The process of claim 1 wherein the intermediate compartment is charged with an aqueous solution comprising TMAH which has been used in the production of 4-aminodiphenylamine for a number of reaction cycles and which contains aniline.

8. The process of claim 1 wherein the catholyte compartment is charged with an aqueous solution of a quaternary ammonium hydroxide which is the same as the quaternary ammonium hydroxide present in the composition to be purified.

9. The process of claim 1 wherein the catholyte compartment is charged with an aqueous 5 to 25 wt % TMAH solution.

10. The process of claim 1 wherein a three-compartment electrolysis cell is used.

11. The process of claim 1 wherein the electrolysis is stopped once a pH of 1 to 7 is reached in the intermediate compartment.

12. The process of claim 1 wherein the electrolysis is stopped once a pH of 4 to 7 is reached in the intermediate compartment.

13. The process of claim 1 wherein identical cation selective membranes are used.

14. The process of claim 1 wherein the cation selective membranes are perfluorinated membranes.

15. The process of claim 1 wherein the intermediate compartment is washed with a suitable solvent.

16. The process of claim 15 wherein the solvent is aniline.

17. The process of claim 15 wherein after washing with a suitable solvent, the intermediate compartment is washed with water.

18. The process of claim 15 wherein the intermediate compartment is washed with aniline followed by washing with water.

19. The process of claim 1 wherein the process is carried out batchwise.

20. The process of claim 19 wherein the intermediate compartment is washed with a suitable solvent at the end of the processing of each batch.

* * * * *